United States Patent
May et al.

(10) Patent No.: US 8,771,364 B2
(45) Date of Patent: Jul. 8, 2014

(54) TIBIAL TRAY HAVING A REINFORCING MEMBER

(75) Inventors: Brian M. May, Warsaw, IN (US); Mukesh Kumar, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 1247 days.

(21) Appl. No.: 12/253,259

(22) Filed: Oct. 17, 2008

(65) Prior Publication Data
US 2010/0100190 A1    Apr. 22, 2010

(51) Int. Cl.
    *A61F 2/38* (2006.01)
(52) U.S. Cl.
    USPC ............... 623/20.32; 623/20.33; 623/20.34
(58) Field of Classification Search
    CPC ............... A61F 2/389; A61F 2002/30878
    USPC ............................ 623/20.32–20.34
    See application file for complete search history.

(56) References Cited

U.S. PATENT DOCUMENTS

| | | |
|---|---|---|
| 4,550,448 A | 11/1985 | Kenna |
| 4,822,362 A | 4/1989 | Walker et al. |
| 4,892,547 A | 1/1990 | Brown |
| 5,480,444 A | 1/1996 | Incavo et al. |
| 5,534,027 A | 7/1996 | Hodorek |
| 5,868,797 A | 2/1999 | Pappas et al. |
| 6,179,876 B1 | 1/2001 | Stamper et al. |
| 6,224,632 B1 | 5/2001 | Pappas et al. |
| 7,740,662 B2 * | 6/2010 | Barnett et al. ............ 623/20.33 |
| 2002/0055784 A1 | 5/2002 | Burstein et al. |
| 2006/0052875 A1 * | 3/2006 | Bernero et al. ............ 623/20.33 |
| 2006/0265079 A1 | 11/2006 | D'Alessio |
| 2007/0010890 A1 | 1/2007 | Collazo |
| 2008/0027557 A1 | 1/2008 | Tuke |
| 2008/0091271 A1 | 4/2008 | Bonitati et al. |
| 2009/0149963 A1 * | 6/2009 | Sekel ..................... 623/20.15 |

FOREIGN PATENT DOCUMENTS

| | | |
|---|---|---|
| DE | 3136636 A1 | 3/1983 |
| DE | 19705733 A1 | 8/1998 |
| FR | 2839442 A1 | 11/2003 |
| JP | H62176447 | 8/1987 |
| JP | H0265858 A | 3/1990 |
| JP | H04122253 | 4/1992 |
| JP | 2003521957 A | 7/2003 |
| JP | 2004237096 A | 8/2004 |
| WO | WO-0025700 A2 | 5/2000 |
| WO | WO-2008048822 A1 | 4/2008 |

OTHER PUBLICATIONS

International Search Report and Written Opinion mailed Dec. 8, 2009 for PCT/US2009/060978, which claims benefit of U.S. Appl. No. 12/253,259, filed Oct. 17, 2008.
International Preliminary Report on Patentability and Written Opinion mailed Apr. 28, 2011 for PCT/US2009/060978, which claims benefit of U.S. Appl. No. 12/253,259, filed Oct. 17, 2008.

(Continued)

*Primary Examiner* — Jason-Dennis Stewart
(74) *Attorney, Agent, or Firm* — Harness, Dickey

(57) ABSTRACT

A knee joint prosthesis can include a tibial component that can have a tibial tray. The tibial tray can include a platform-like tray that defines a superior surface and an inferior surface. The platform-like tray can have a tray perimeter and a raised wall formed on the inferior surface. The raised wall can be offset inboard relative to the tray perimeter. Porous material can be disposed on the inferior surface of the platform-like tray at a location generally between the raised wall and the tray perimeter.

15 Claims, 5 Drawing Sheets

(56) References Cited

OTHER PUBLICATIONS

Office Action mailed Aug. 29, 2013 for Japanese Application 2011-532276 claiming benefit of U.S. Appl. No. 12/253,259, filed Oct. 17, 2008.

Japanese Office Action mailed Apr. 7, 2014 for JP Application No. 2011-532276 filed Apr. 15, 2011, claiming benefit of U.S. Appl. No. 12/579,479, which is a continuation-in-part of U.S. Appl. No. 12/253,259, filed Oct. 17, 2008.

* cited by examiner

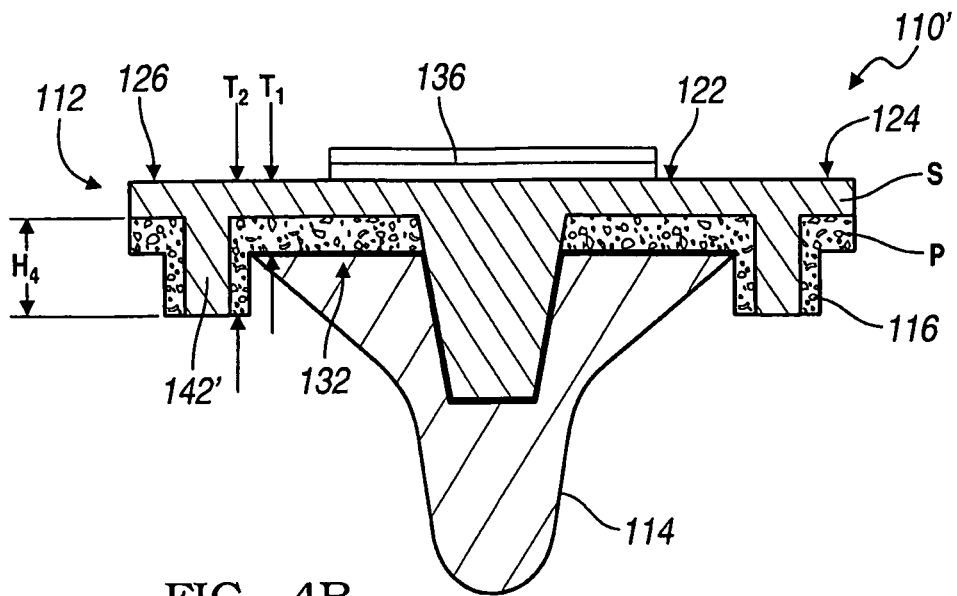
FIG. 4B
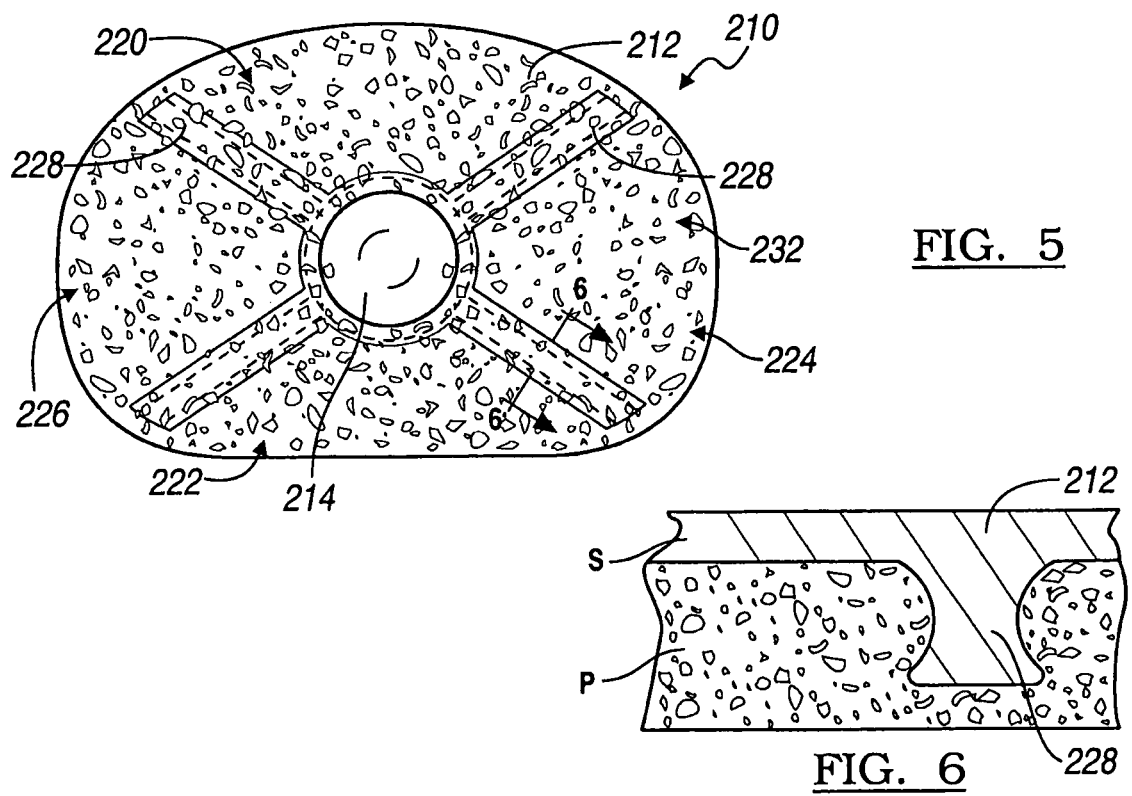
FIG. 5
FIG. 6

TIBIAL TRAY HAVING A REINFORCING MEMBER

FIELD

The present disclosure relates to tibial trays and more particularly to a tibial tray incorporating a reinforcing member.

BACKGROUND

The statements in this section merely provide background information related to the present disclosure and may not constitute prior art.

In some instances, the knee joint may undergo degenerative changes due to multiple etiologies. In some examples, when these degenerative changes are advanced, irreversible and unresponsive to non-operative management, it may ultimately become necessary to replace some or all of the natural knee joint with knee joint prosthetics. In one example, a knee joint prosthesis can comprise a femoral component and a tibial component. The femoral component and the tibial component can be designed to be surgically attached to the distal end of the femur and the proximal end of the tibia, respectively. The femoral component can further be designed to cooperate with the tibial component in simulating the articulating motion of an anatomical knee joint.

Typically, the tibial component can include a substantially planar platform-like tibial tray and an inferiorly extending tibial stem. The tibial stem can be adapted to be received in a corresponding opening made by a surgeon in the longitudinal center of the tibia. In general, it can be desired to provide a tibial tray having sufficient fatigue strength as well as providing an area for bone fixation.

SUMMARY

A knee joint prosthesis can include a tibial component that can have a tibial tray. The tibial tray can include a platform-like tray that defines a superior surface and an inferior surface. The platform-like tray can have a tray perimeter and a raised wall formed on the inferior surface. The raised wall can be offset inboard relative to the tray perimeter. Porous material can be disposed on the inferior surface of the platform-like tray at a location generally between the raised wall and the tray perimeter. The porous material can also be disposed inboard of the raised wall on the inferior surface of the platform-like tray.

According to additional features, the raised wall of the tibial tray can define an outer profile that substantially matches the tray perimeter. The tibial component can further comprise a stem that extends inferiorly from the platform-like tray. The porous material can be disposed in a location generally between the raised wall and the stem. According to one example, the platform-like tray and the raised wall can be integrally formed of solid biocompatible material. The raised wall can be adapted to engage cancellous bone and the porous material can be adapted to engage cortical bone in an implant position.

According to additional features, the porous material can define a first thickness at the tray perimeter and a second thickness at the raised wall. The second thickness can be greater than the first thickness. According to one example, the platform-like tray can further comprise a first support wall formed on the inferior surface and extending between a generally anterior/lateral position to a posterior/medial position. The platform-like tray can also include a second support wall formed on the inferior surface and extending between a generally anterior/medial position to a posterior/lateral position. According to various examples, the first and second support walls can define a generally dove-tail cross-section. The knee joint prosthesis can additionally comprise a femoral component and a bearing selectively coupled to the tibial component.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 4B is a cross-sectional view of a tibial tray constructed in accordance to additional features of the present disclosure;

FIG. 5 is an inferior view of another tibial tray constructed in accordance to additional features of the present disclosure;

FIG. 6 is a cross-sectional view of the tibial tray of FIG. 5 and taken along line 6-6;

DETAILED DESCRIPTION

The following description is merely exemplary in nature and is not intended to limit the present disclosure, its application, or uses.

Figure 1:
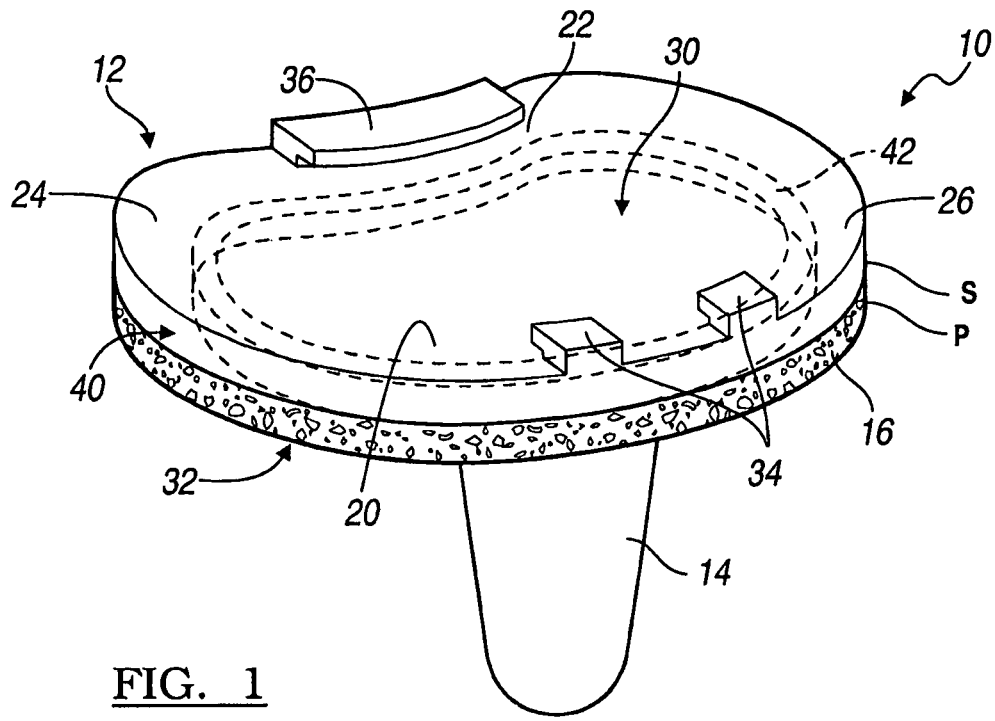
FIG. 1 is an anterior perspective view of an exemplary tibial tray constructed in accordance with one example of the present teachings.

With initial reference now to FIG. 1, a tibial component constructed according to the present teachings is shown and generally identified at reference numeral 10. The tibial component 10 can generally include a substantially planar platform-like tray 12 having a modular, inferiorly extending tibial stem 14. In other examples, the stem 14 can be integrally formed with the tibial tray 12. The tibial stem 14 can be adapted to be received in a corresponding opening made by a surgeon in a proximal tibia. The tibial component 10 according to the present teachings incorporates porous material 16 at selected areas as will be described. As will become appreciated from the following discussion, the tibial component 10 constructed in accordance to the present teachings can increase a fatigue strength of the tibial tray 12 while simultaneously maximizing the volume of porous material 16 intended for bone fixation. The tibial tray 12 can provide a solid substrate portion S and a porous material portion P.

For discussion purposes, the tibial component 10 will be described for use with a knee joint having a surgically resected left tibia. It is understood, however, that the tibial component 10 may be universal, such that it may be adapted for use with a surgically resected right tibia. Likewise, the tibial component 10 may be adapted for use in either a left or a right tibia. The tibial tray 12 can generally define an anterior portion 20, a posterior portion 22, a medial portion 24, and a lateral portion 26. The tibial tray 12 can generally define a superior bearing engaging surface 30 and an inferior bone engaging surface 32 (see also FIG. 2).

Figure 11:
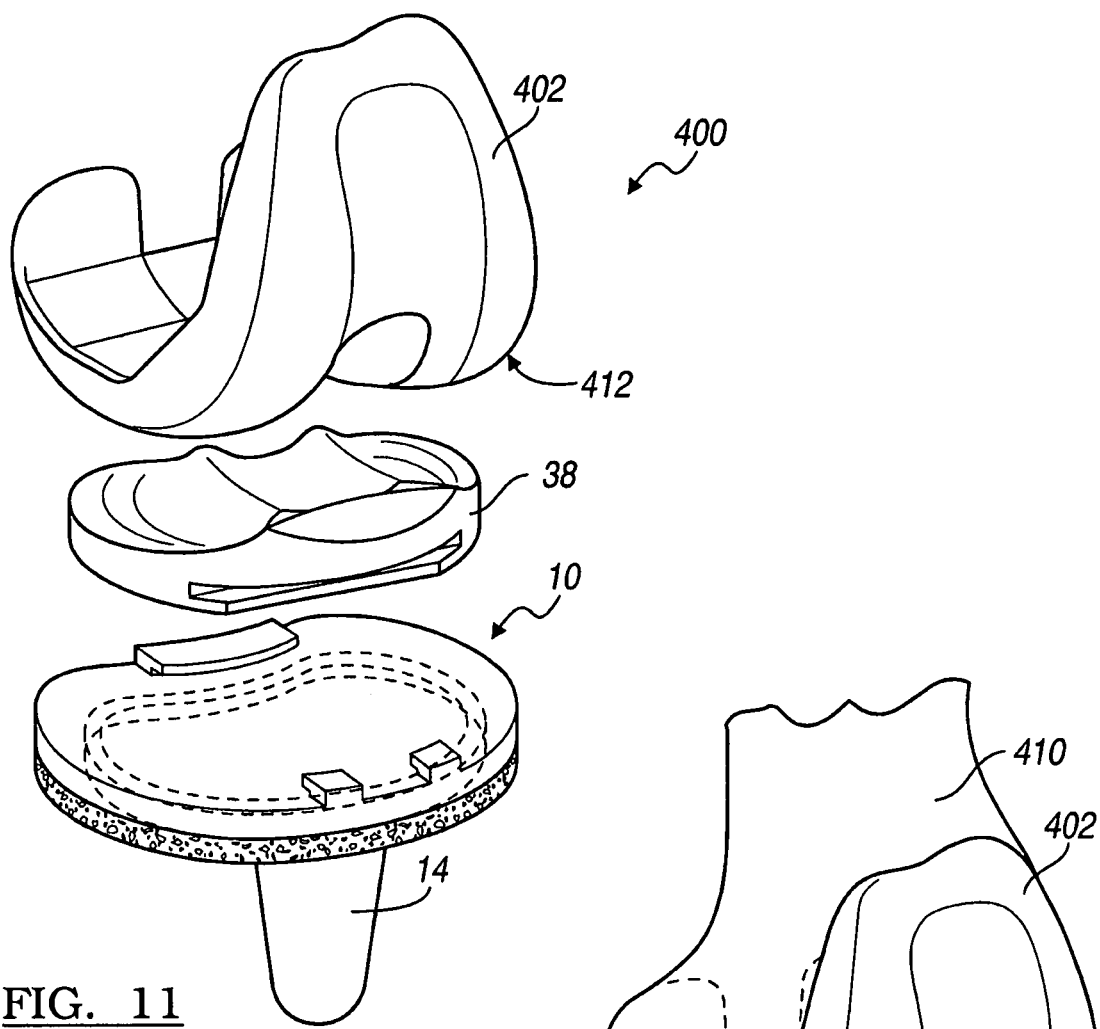
FIG. 11 is an exploded anterior view of a knee joint prosthesis including the tibial tray shown in FIG. 1 according to the present disclosure.
Figure 12:
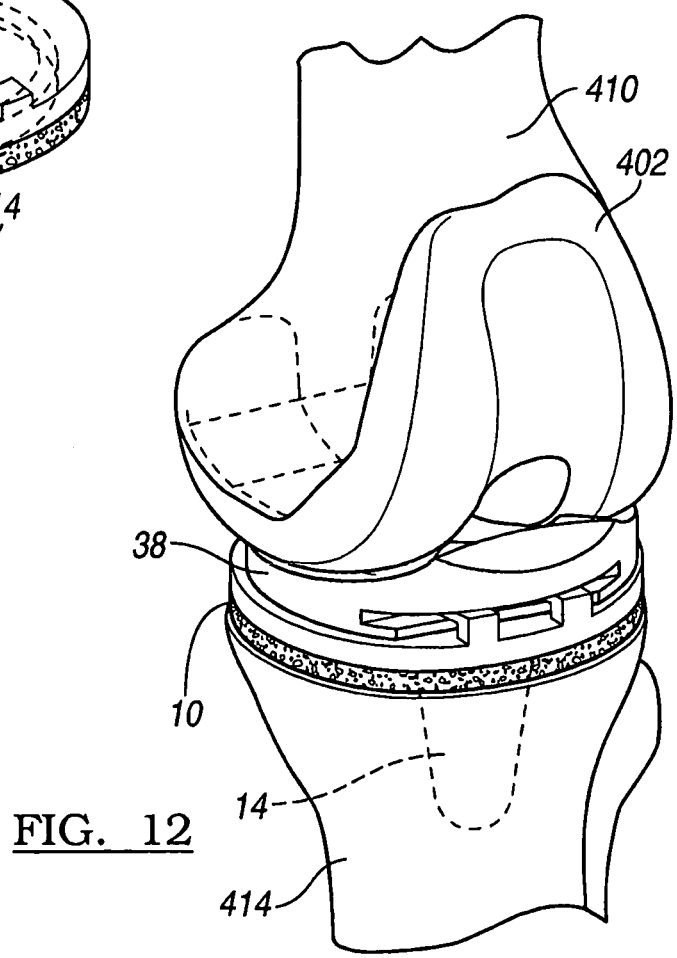
FIG. 12 is an anterior perspective view of the knee joint prosthesis of FIG. 11 and shown in an implanted position with a surgically prepared femur and tibia according to the present disclosure.

The exemplary tibial tray 12 can define a pair of integrally formed posts 34, which extend superiorly at the anterior portion 20. A catch 36 can also be defined at the posterior portion 22. The posts 34 may cooperate with a locking bar (not specifically shown) to secure a tibial bearing 38 (FIGS. 11 and 12). In this way, the posts 34 and catch 36 can be used to secure a tibial bearing 38 to the tibial tray 12. It is appreciated that other retaining features may be employed for securing a tibial bearing 38 to the tibial tray 12. Likewise, it is appreciated, that the tibial tray 12 may alternatively be adapted for use with a floating bearing. In such an example, the superior surface 30 may be highly polished to provide a substantially smooth tibial bearing surface. While not specifically shown, a floating bearing having a substantially planar inferior bearing surface may be located above the tibial tray 12. In this way, the floating bearing may slidably move relative to the highly polished superior surface 30 of tibial tray 12. The tibial tray 12 may be adapted for use in a cruciate retaining (CR) knee replacement, a posterior stabilized (PS) knee replacement and a fully constrained knee replacement for example.

Figure 2:
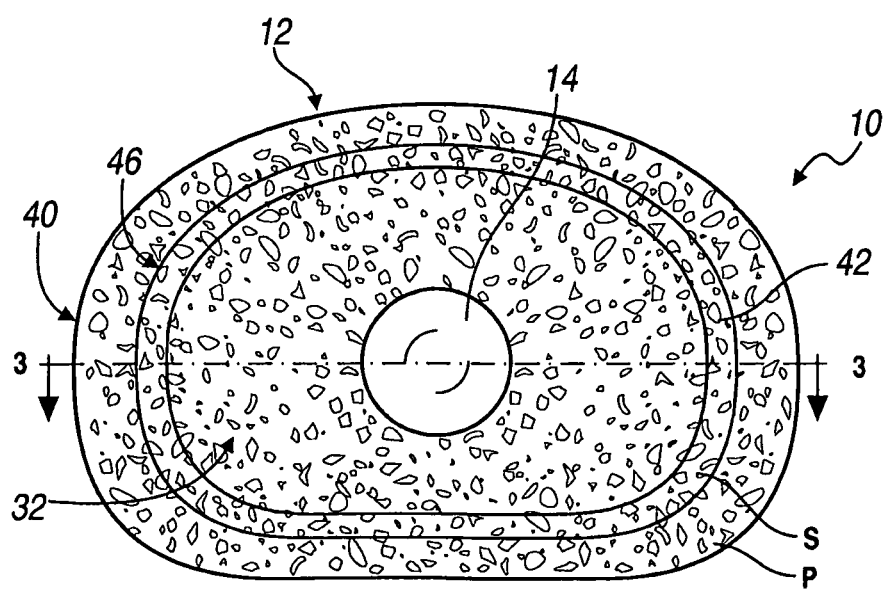
FIG. 2 is an inferior view of the tibial tray of FIG. 1.
Figure 3:
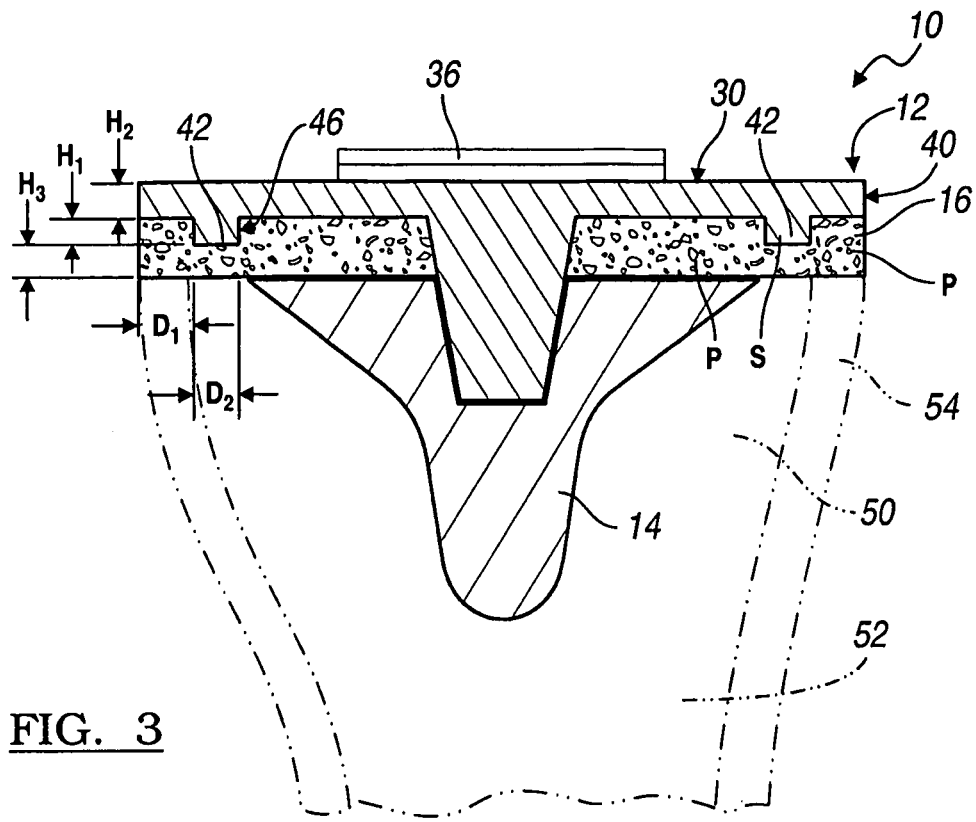
FIG. 3 is a cross-sectional view of the tibial tray of FIG. 2 taken along line 3-3 and shown implanted into an exemplary tibia.

With continued reference to FIG. 1 and additional reference now to FIGS. 2-4, additional features of the tibial tray 12 will be described in greater detail. In general, the tibial tray 12 can define a tray perimeter 40 and a raised wall 42. The raised wall 42 can be a closed wall formed around the inferior surface 32 of the tibial tray 12. In one example, the raised wall 42 can be integrally formed with the tibial tray 12 as a whole. The tibial tray 12 and the raised wall 42 can collectively define the solid substrate portion S. Explained differently, the raised wall 42 can be monolithic or one-piece with the tibial tray 12. In one example, the solid substrate portion S, including the tray 12 and the raised wall 42 (and in some examples, the stem 14) can be formed of solid biocompatible material, such as, but not limited to titanium. The solid biocompatible material portions of the tray 12 can be formed by any suitable means, such as by machining, molding, casting or other methods.

According to the present teachings, the raised wall 42 can be offset inboard relative to the tray perimeter 40. As will be described in more detail, the raised wall 42 can be offset inboard a suitable distance to engage a cancellous bone 50 of a tibia 52. In this way, the porous material portion 16 can be arranged between the raised wall 42 and the tray perimeter 40 (FIG. 3). The configuration of the tibial tray 12 can provide porous material 16 outboard of the raised wall 42 in areas that can engage cortical bone 54 of the tibia 52. As best shown in FIG. 2, the raised wall 42 can define a wall perimeter 46 that is stepped inboard (in a direction toward the stem 14), a substantially equivalent distance around the inferior surface 32 of the tibial tray 12 relative to the tray perimeter 40.

Furthermore, the raised wall 42 can be formed inboard to provide rigidity to a tray that can be formed thinner versus a tray without a ridge.

With specific reference now to FIG. 3, exemplary dimensions of the tibial tray 12 will be described. In one example, the raised wall 42 can be offset inboard relative to the tray perimeter 40 a distance $D_1$ to provide mechanical strength (such as a sufficient stiffness or tensile strength). The raised wall 42 can define a lateral thickness $D_2$. In one example, $D_1$ can be about 2-3 mm. It is appreciated that $D_1$ can vary slightly (i.e., the distance between the tray perimeter 40 and the wall perimeter 46) around the tibial tray 12. The distance $D_2$ can be about 2-4 mm. The porous material 16 can define a total height of height $H_1$ plus height $H_3$. In one example, the height $H_1$ can be substantially equivalent to a height of the raised wall 42. The height $H_1$ plus $H_3$ can be greater than a thickness of the solid substrate portion $H_2$ of the tibial tray 12. Again, those skilled in the art will appreciate that these dimensions are merely exemplary. These dimensions can be optimized, such that the raised wall 42 can be positioned at an area suitable to cooperate with the cancellous bone 50 of a particular patient. Consequently, the porous material 16 can be optimized to interface with the cortical bone 54 of a particular patient.

In general, maximum flexion of the tibial tray 12 can occur at its periphery. When implanted, this flexion generally does not materialize due to the support of the surrounding cortical bone 50 of the tibia 52. The configuration of the raised wall 42 and the porous material 16 according to the present teachings can allow for deeper bone ingrowth due to maximum loading of the surrounding cortical bone 54. In one example, the configuration and placement of the raised wall 42 can allow for thinner thicknesses of the tibial tray 12 because of the increased rigidity the raised wall 42 can provide.

Figure 4A:
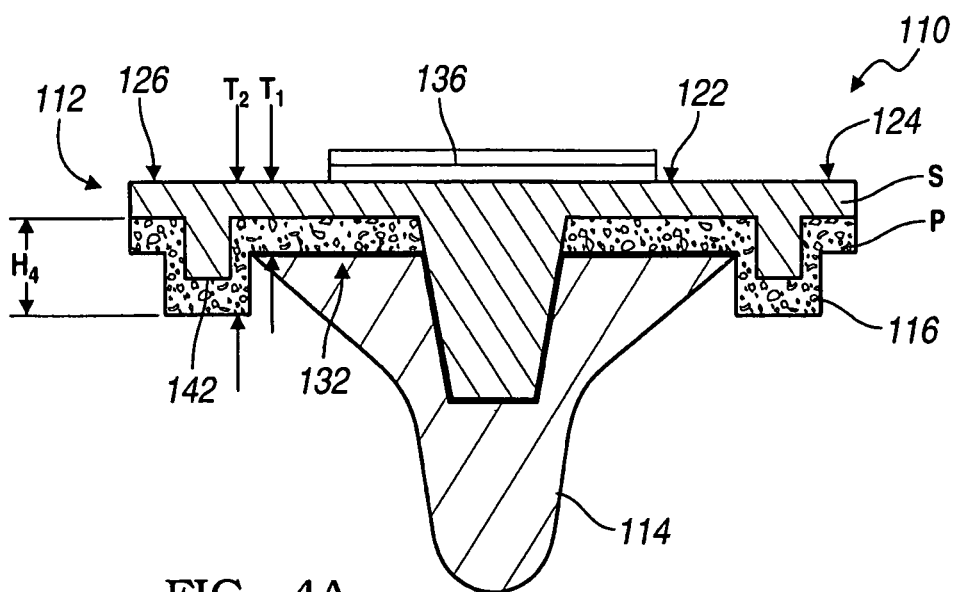
FIG. 4A is a cross-sectional view of a tibial tray constructed in accordance to additional features of the present disclosure.

Turning now to FIG. 4A, a tibial component 110 constructed in accordance to additional features is shown. The tibial component 10 can include a substantially planar platform-like tibial tray 112 having an inferiorly extending tibial stem 114. The tibial component 110 can incorporate porous material 116. The tibial tray 112 can provide a solid substrate portion S and a porous material portion P. The tibial tray 112 can define a medial portion 124 and a lateral portion 126. A catch 136 can be defined on a posterior portion 122. A raised wall 142 can be defined around an inferior surface 132 of the tibial tray 112 similar to that described above with respect to the tibial tray 12. In the tibial tray 112, shown in FIG. 4A, the raised wall 142 and the porous material 116 can collectively define a height $H_4$. The height $H_4$ can be greater than the height $H_1$ plus $H_3$ described with respect to the tray 12 (see FIG. 3). In one example, the height $H_2$ can be between 2-4 mm. As can be appreciated, the raised wall 142 having an increased height of $H_4$ can provide increased fatigue strength of the tray 112 as a whole. As shown in FIG. 4A, the porous material 116 can have a first thickness $T_1$ and a second thickness $T_2$. In one example, the thickness $T_1$ can be substantially about 2-3 mm and the thickness $T_2$ can be substantially about 2-4 mm. Again, those skilled in the art will appreciate that these diameters are merely exemplary. Other dimensions and ranges are contemplated. A tibial component 110' shown in FIG. 4B is constructed in accordance to additional features. The tibial component 110' is constructed similar to the tibial component 110 (FIG. 4A) except a raised wall 142' extends the length of $H_4$ (i.e. no porous material 116 is provided on an inferior surface of the raised wall 142').

The porous material 16, 116 can be any metal or alloy that is suitable for use in an implant and provide the desired strength and load bearing capability according to a particular application. Suitable exemplary metals can include titanium, cobalt, chromium, or tantalum, alloys thereof, stainless steel, and combinations thereof. One suitable porous metal and method for making the same may be found in commonly owned and copending U.S. Ser. No. 11/357,929, filed Feb. 17, 2006, entitled "Method and Apparatus for Forming Porous Metal Implants", which is expressly incorporated by reference.

The porous material portion P (i.e., porous material 16,116) can be attached to the solid substrate portion S of the tibial tray 12 by any suitable means, such as welding, sintering, using a laser, etc. In various embodiments, the solid substrate portion S of the tibial tray 12 can be formed of metal, such as the same metal as the porous material portion P. The solid substrate portion S of the tibial tray 12 can be prepared prior to attaching the porous material portion P. The solid substrate portion S of the tibial tray 12 can be acid etched, subjected to an acid bath, grit blasted, or ultrasonically cleaned for example. Other preparations can include adding channels, pits, grooves, indentations, bridges, or holes into the solid substrate portion S of the tibial tray 12. These additional features may increase the attachment of the porous portion P to the solid substrate portion S of the tibial tray 12.

Additional agents can be coated onto or in at least a surface of the porous material 16. Agents can include resorbable ceramics, resorbable polymers, antibiotics, demineralized bone matrix, blood products, platelet concentrate, allograft, xenograft, autologous and allogeneic differentiated cells or stem cells, nutrients, peptides and/or proteins, vitamins, growth factors, and mixtures thereof, which would facilitate ingrowth of new tissue into the porous material 16.

With reference now to FIG. 5, a tibial component 210 constructed in accordance to additional features is shown. The tibial component 210 can include a substantially planar platform-like tibial tray 212 having an inferiorly extending tibial stem 214. The tibial tray 212 can define an anterior portion 220, a posterior portion 222, a medial portion 224, and a lateral portion 226. A pair of support walls 228 can be defined across the inferior surface 232 of the tibial tray 212. According to the example shown, one of the support walls 228 can extend from an anterior/lateral position to a posterior/medial position. The other support wall 228 can extend from an anterior/medial position to a posterior/lateral position. As best shown in FIG. 6, a cross-section of the support wall 228 can define a generally dove-tail shape. It is appreciated that the raised wall 42 (FIG. 2) and/or 142 (FIG. 4) can define a dove-tail shape. The tibial tray 212 can provide a solid substrate portion S and a porous material portion P. In one example, such as shown in FIG. 6, the porous material portion P can extend inferiorly beyond the support wall 228. In another example, the porous material portion P may not extend inferiorly beyond the support wall 228 (such as shown in FIG. 3).

Figure 7:
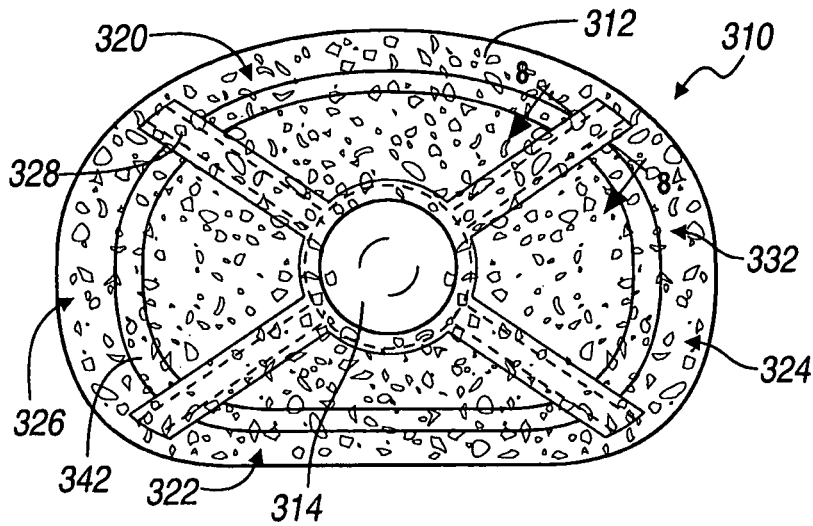
FIG. 7 is an inferior view of a tibial tray constructed in accordance to additional features of the present disclosure.
Figure 8:
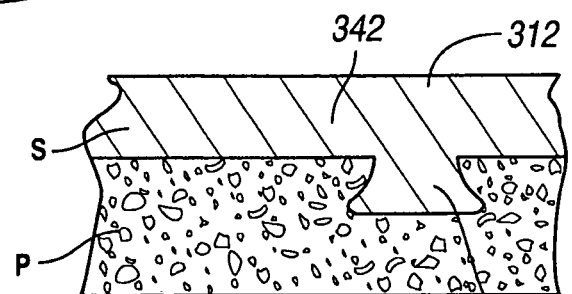
FIG. 8 is a cross-sectional view of the tibial tray of FIG. 7 and taken along line 8-8.
Figure 9:
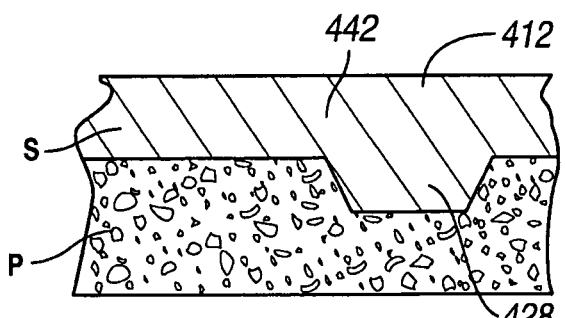
FIG. 9 is a cross-sectional view of another tibial tray illustrating a support wall having an alternate cross-section.
Figure 10:
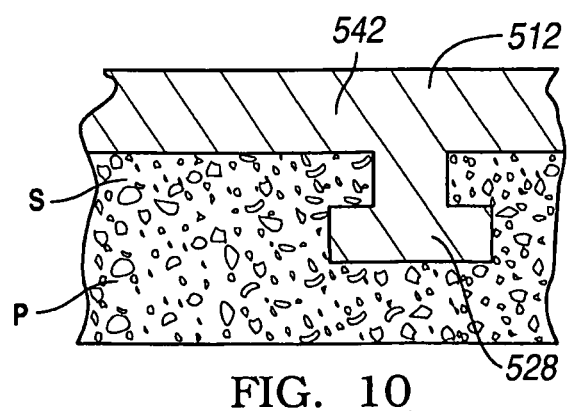
FIG. 10 is a cross-sectional view of yet another tibial tray illustrating a support wall having an alternate cross-section.

Turning now to FIGS. 7 and 8, a tibial component 310 constructed in accordance to additional features is shown. The tibial component 310 can include a substantially planar platform-like tibial tray 312 having an inferiorly-extending tibial stem 314. The tibial tray 312 can define an anterior portion 320, a posterior portion 322, a medial portion 324, and a lateral portion 326. The tibial tray 312 of FIG. 7 can define a pair of support walls 328, such as described above in relation to the tibial tray 212 of FIG. 5. The tibial tray 312 can further define a raised wall 342. The raised wall 342 can be constructed, such as described above with respect to the raised wall 42 of the tibial tray 12 (FIGS. 1-3). According to some examples, the relative offsets and thicknesses of the raised wall 342 and the porous material portion P can be similar to those described in relation to FIGS. 3 and 4 above. FIG. 9 illustrates a tibial tray 412 having a raised wall 442 that includes support walls 428. FIG. 10 illustrates a tibial tray 512 having a raised wall 542 that includes support walls 528.

With reference now to FIGS. 11 and 12, the tibial component (or 110, 210, or 310) can be used as part of a total knee prosthesis 400. In one example, the total knee prosthesis 400 can include a femoral component 402, the tibial component 10, and the bearing 38. As is known, the femoral component 402 can be rigidly connected to a distal end of a femur 410 (FIG. 12) after the femur 410 has been resected in a manner, which is well known in the art. The femoral component 402 can include a condylar portion 412, which engages the bearing 38. The tibial component 10 can be connected to a tibia 414 (FIG. 12) by any suitable method. The bearing 38 can be made from any suitable material, such as ultra-high molecular weight polyethylene (UHMWP). The total knee prosthesis 400 can be part of any knee joint, such as, but not limited to, cruciate retaining (CR), posterior stabilized (PS), and fully constrained (FC).

Those skilled in the art can now appreciate from the foregoing description that the broad teachings of the present disclosure can be implemented in a variety of forms. Therefore, while this disclosure has been described in connection with particular examples thereof, the true scope of the disclosure should not be so limited since other modifications will become apparent to the skilled practitioner upon a study of the drawings, the specification and the following claims.

What is claimed is:

1. A knee joint prosthesis comprising:
a tibial component including a tibial tray, said tibial tray comprising:
a platform-like tray having a superior bearing engaging surface and an inferior surface, said platform-like tray defining a tray perimeter and a first height measured between said superior bearing engaging surface and said inferior surface;
a raised wall formed on and extending from said inferior surface of said platform-like tray, said raised wall offset inboard relative to said tray perimeter and configured to provide increased rigidity of said platform-like tray; and
porous material disposed on said inferior surface of said platform-like tray at a location generally between said raised wall and said tray perimeter, said porous material having a second height measured between said inferior surface of said platform-like tray and a bone engaging surface of said porous material, said second height being greater than said first height;
wherein said platform-like tray further comprises, a first support wall formed on said inferior surface and extending between a generally anterior/lateral position to a posterior/medial position.

2. The knee joint prosthesis of claim 1 wherein said raised wall is a closed wall that defines an outer profile that substantially matches said tray perimeter.

3. The knee joint prosthesis of claim 2 wherein said tibial component further comprises, a stem that extends inferiorly from said platform-like tray.

4. The knee joint prosthesis of claim 3 wherein said porous material is disposed in a location generally between said raised wall and said stem.

5. The knee joint prosthesis of claim 1 wherein said platform-like tray and said raised wall are integrally formed of solid biocompatible material selected from the group comprising metal, PEEK, fiber-reinforced PEEK and ceramic.

6. The knee joint prosthesis of claim 1 wherein said raised wall is perpendicular relative to a plane define by said platform-like tray and is configured to be aligned with cancellous bone and said porous material is configured to abut cortical bone in an implanted position.

7. The knee joint prosthesis of claim 1 wherein said platform-like tray further comprises, a second support wall formed on said inferior surface and extending between a generally anterior/medial position to a posterior/lateral position.

8. The knee joint prosthesis of claim 7 wherein said first and second support walls define a generally dove-tail cross-section.

9. The knee joint prosthesis of claim 1, further comprising:
a femoral component; and
a bearing selectively engageable with said tibial component.

10. A knee joint prosthesis comprising:
a tibial component including a tibial tray, said tibial tray comprising:
a solid metal portion comprising:
a platform-like tray having a superior bearing engaging surface and an inferior surface, said platform-like tray defining a tray perimeter;
a stem extending inferiorly from said platform-like tray;
a raised wall formed on said inferior surface and extending to a bone engaging end face, said raised wall offset toward said stem and defining a closed wall having a profile that is substantially equivalent to said tray perimeter around said inferior surface; and
a porous metal portion comprising:
a first porous metal portion disposed on said inferior surface of said platform-like tray outboard of said raised wall;
a second porous metal portion disposed inboard of said raised wall, wherein said first and second porous metal portions are discontinuous at said bone engaging end face such that said bone engaging end face is free of porous metal and configured to directly engage bone;
wherein said platform-like tray further comprises, first and second support walls formed on said inferior surface and extending radially therealong.

11. The knee joint prosthesis as claimed in claim 10 wherein said first porous metal portion is disposed from said raised wall to said tray perimeter.

12. The knee joint prosthesis as claimed in claim 10 wherein said second porous metal portion is disposed from said raised wall to said stem.

13. The knee joint prosthesis as claimed in claim 10 wherein said raised wall is configured to be aligned with cancellous bone and said first porous metal portion is configured to abut cortical bone in an implanted position.

14. The knee joint prosthesis of claim 10 wherein at least one of said first and second support walls defines a generally dove-tail cross-section.

15. The knee joint prosthesis of claim 10, further comprising:
a femoral component; and
a bearing selectively coupled to said tibial component.

* * * * *